United States Patent
Pavlidis et al.

(10) Patent No.: US 7,111,980 B2
(45) Date of Patent: Sep. 26, 2006

(54) SYSTEM AND METHOD USING THERMAL IMAGE ANALYSIS AND SLOPE THRESHOLD CLASSIFICATION FOR POLYGRAPH TESTING

(75) Inventors: Ioannis Pavlidis, Minneapolis, MN (US); James A. Levine, Rochester, MN (US)

(73) Assignee: Honeywell International Inc., Morristown, NJ (US)

(*) Notice: Subject to any disclaimer, the term of this patent is extended or adjusted under 35 U.S.C. 154(b) by 784 days.

(21) Appl. No.: 10/008,786

(22) Filed: Nov. 13, 2001

(65) Prior Publication Data

US 2003/0016726 A1 Jan. 23, 2003

Related U.S. Application Data

(60) Provisional application No. 60/285,004, filed on Apr. 19, 2001.

(51) Int. Cl.
*G01K 13/00* (2006.01)
*A61B 5/02* (2006.01)

(52) U.S. Cl. .................. 374/45; 374/121; 374/129; 600/407

(58) Field of Classification Search .......... 374/121, 374/129, 45; 600/407
See application file for complete search history.

(56) References Cited

U.S. PATENT DOCUMENTS

| | | | |
|---|---|---|---|
| 2,944,542 A | | 7/1960 | Barnett et al. |
| 3,847,142 A | | 11/1974 | Williams Jr. et al. |
| 4,403,615 A | * | 9/1983 | Hoehner .................. 128/692 |

(Continued)

FOREIGN PATENT DOCUMENTS

| | | |
|---|---|---|
| EP | 0867830 A | 9/1998 |
| EP | 0 885 587 A1 | 12/1998 |
| WO | 9216910 A | 10/1992 |
| WO | WO 9808431 A | 3/1998 |
| WO | 9906974 A | 2/1999 |

OTHER PUBLICATIONS

Measuring Intelligence. www.bbc.co.uk/science/hottopics/intelligence/iq.shtml. Apr. 2002.*

Fendt et al., "The neuroanatomical and neurochemical basis of conditioned fear," *Neurosci Biobehav Rev*, 23(5):743–60 (May, 1999).

Fujimasa et al., "Converting Far-Infrared Image Information to Other Physiological Data," *IEEE Engineering in Medicine and Biology*, vol. 19, No. 3, pp. 71–75, 2000.

Gose et al., "Pattern Recognition and Image Analysis," pp. 159–186, Prentice Hall, Upper Saddle River, New Jersey (1996).

Holden, "Panel Seeks Truth in Lie Detector Debate," *Science*, vol. 291, No. 9, p. 967,2001.

Iwatani, "An Estimation Method of Skin Blood Flow Rate Using Heat Flow Analysis," *Japanese Journal of Medical Electronics and Biological Engineering*, vol. 20, No. 3, pp. 249–255, includes English Abstract, 1982.

(Continued)

*Primary Examiner*—Gail Verbitsky
(74) *Attorney, Agent, or Firm*—Kris T. Fredrick

(57) ABSTRACT

Thermal image data of at least a region of a face of a person is provided. The thermal image data is transformed to blood flow rate data which includes a slope representative of the change of blood flow rate over time. The slope is compared to a slope threshold to determine a physiological state of the person. For example, it may be determined whether the person is deceptive or non-deceptive, e.g., deceptive with respect to an elicited response from the person.

31 Claims, 8 Drawing Sheets

U.S. PATENT DOCUMENTS

| | | | |
|---|---|---|---|
| 4,500,784 A | | 2/1985 | Hacskaylo |
| 4,520,504 A | | 5/1985 | Walker et al. |
| 5,013,917 A | | 5/1991 | Ulich |
| 5,099,852 A | | 3/1992 | Meister et al. |
| 5,221,919 A | | 6/1993 | Hermans |
| 5,339,817 A | | 8/1994 | Nilsson |
| 5,361,769 A | | 11/1994 | Nilsson |
| 5,363,311 A | * | 11/1994 | Garbo .................. 364/481 |
| 5,370,121 A | * | 12/1994 | Reichenberger et al. .............. 128/660.02 |
| 5,406,956 A | * | 4/1995 | Farwell ................ 128/731 |
| 5,507,291 A | * | 4/1996 | Stirbl et al. .......... 128/653.1 |
| 5,703,367 A | | 12/1997 | Hashimoto et al. |
| 5,771,261 A | | 6/1998 | Anbar |
| 5,774,571 A | | 6/1998 | Marshall |
| 5,860,922 A | | 1/1999 | Gordon et al. |
| 5,860,935 A | * | 1/1999 | Blaszynski et al. ......... 600/547 |
| 5,876,334 A | * | 3/1999 | Levy ...................... 600/300 |
| 5,900,942 A | | 5/1999 | Spiering |
| 5,940,139 A | | 8/1999 | Smoot |
| 6,002,505 A | | 12/1999 | Kraenert et al. |
| 6,464,646 B1 | | 10/2002 | Shalom et al. |
| 2002/0062089 A1 | * | 5/2002 | Johnson Jr. ................ 600/544 |
| 2002/0091336 A1 | * | 7/2002 | Cohen ...................... 600/547 |
| 2002/0183627 A1 | * | 12/2002 | Nishii et al. ............... 600/485 |

OTHER PUBLICATIONS

Jacquez et al., "The spectral reflectance of human skin in the region 0.7–2.6 μm," *Technical Report, 189*, Army Medical Research Laboratory, Fort Knox (Apr., 1955).

Jordan et al., "Hierarchical Mixtures of Experts and the EM Algorithm," *Neural Computation, 6*, pp. 181–214 (1994).

Levine et al., "The energy expended in chewing gun," *New England Journal of Medicine*, 341(27):2100 (Dec., 1999).

Levine et al., "Face of Fear", *The Lancet*, vol. 357, No. 9270, Jun. 2, 2001.

Mendez, *The Master of Disguise*, William Morrow and Co., New York, N.Y.; cover page, title page, copyright page and table of contents only; 4 pp. (1999).

Moghaddam et al., "Probabilistic Visual Learning for Object Recognition," *IEEE Trans. Pattern Analysis and Machine Intelligence*, 19(7):696–710 (Jul., 1997).

Otsu, "A Threshold Selection Method from Gray–Level Histograms," *IEEE Trans. Systems, Man And Cybernetics*, 9:62–65 (Jan., 1979).

Pavlidis et al., "Automatic passenger counting in the high occupancy vehicle (HOV) lanes" *Proceedings 1999 Annual Meeting of the Intelligent Transportation Society of America*, Washington, D.C. (Apr. 19–22, 1999).

Pavlidis et al., "A near–infrared fusion scheme for automatic detection of vehicle passengers," *Proceedings 1999 IEEE Workshop on Computer Vision Beyond the Visible Spectrum: Methods and Applications*, 41–48, Fort Collins, C.O. (Jun. 22, 1999).

Pavlidis et al., "Automatic Detection of Vehicle Occupants– The Imaging Problem and Its Solution," *Machine Vision and Applications*, vol. 11, No. 6, pp. 313–320, 2000.

Pavlidis et al., "Monitoring of Periorbital Blood Flow Rate Through Thermal Image Analysis and its Application to Polygraph Testing", Proceedings $23^{rd}$ Annual International Conference of the IEEE Engineering in Medicine and Biology Society, Instanbul, Turkey, Oct. 25–28, 2001.

Pavlidis et al., "Thermal Imaging for Anxiety Detection", *2000 IEEE Workshop on Computer Vision Beyond the Visible Spectrum: Methods and Applications*, pp. 104–109, Hilton Head Island, South Carolina, Jun. 16, 2000.

Penev et al., "Local feature analysis: a general statistical theory for object representation," *Network: Computation in Neural Systems*, 7(3):477–500 (Aug., 1996).

Pentland et al., "Face recognition for smart environments," *IEEE Computer*, 33(2):50–55 (Feb., 2000).

Phillips et al., "The FERET database and evaluation procedure for face–recognition algorithms," *Image and Vision Computing*, 16(5):295–306 (Apr., 1998).

Prokoski "Disguise detection and identification using infrared imagery," *Proceedings of SPIE, Optics, and Images in Law Enforcement II*, 339:27–31, A.S. Hecht, ed., Arlington, V.A. (May, 1982).

Sabins, *Remote Sensing, Principles and Interpretation*, W.H. Freeman and Company, New York, N.Y.; cover page, title page, copyright page and table of contents only; 7 pgs. (1997, 3rd ed.).

Sliney, "Laser and LED eye hazards: safety standards," *Optics and Photonics News*, pp 32–(Sep., 1997).

Visionics Corporation, "Face detection constantly searches for faces in a datastream" Jersey City, N.J., retrieved from the Internet on Jun. 25, 2001, <URL:http://www.visionics.com/facit/tech/detect.html>, 1 p.

Wiskott et al., "Face recognition by elastic bunch graph matching," *IEEE Trans. Pattern Analysis and Machine Intelligence*, 19(7):775–779 (Jul., 1997).

Zhu et al., "Region Competition: Unifying Snakes, Region Growing, and Bayes/MDL for Multiband Image Sementation," IEEE Transactions on Image Analysis and Machine Intelligence, 18(9) (Sep., 1996). 884–900.

* cited by examiner

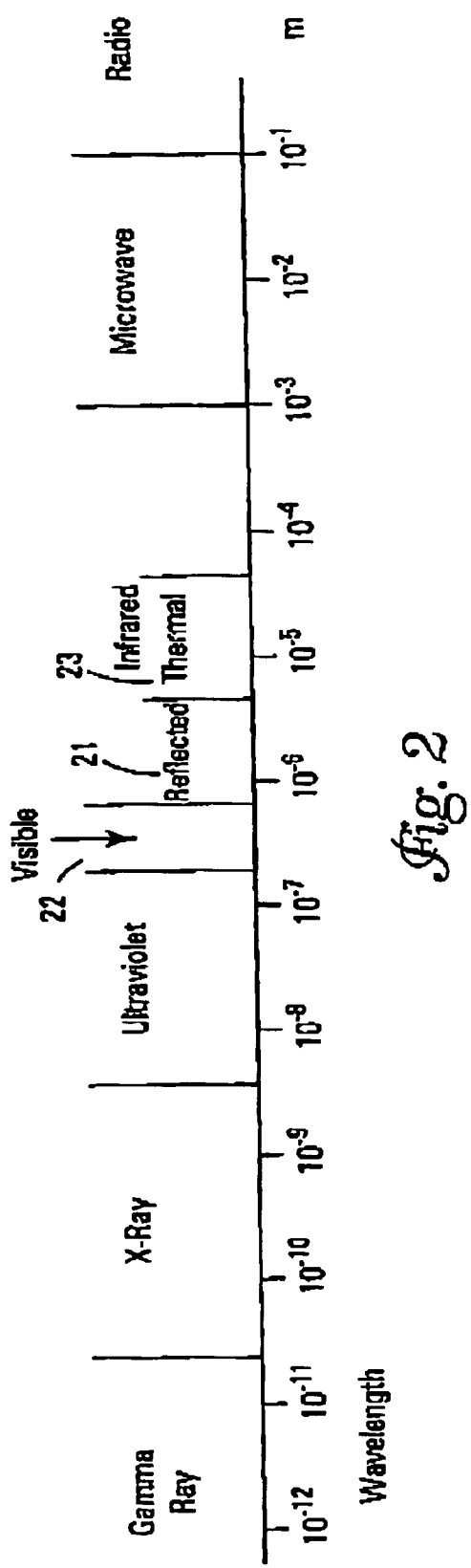

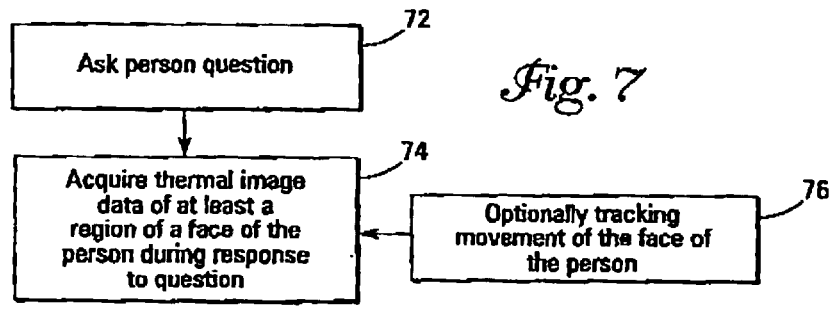
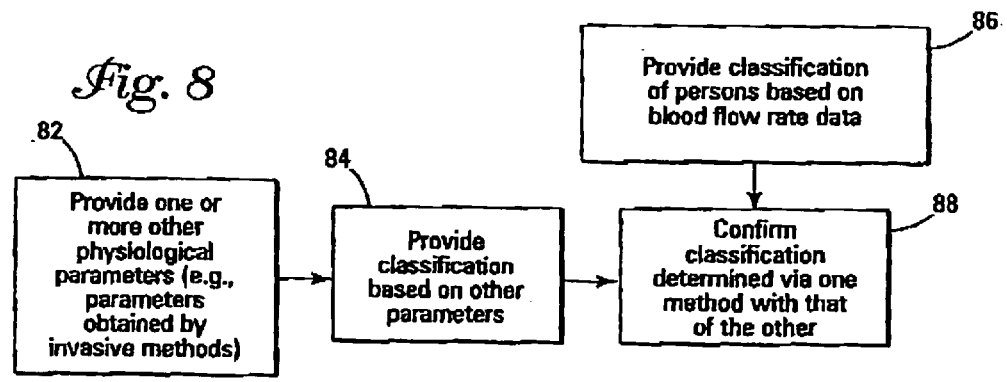
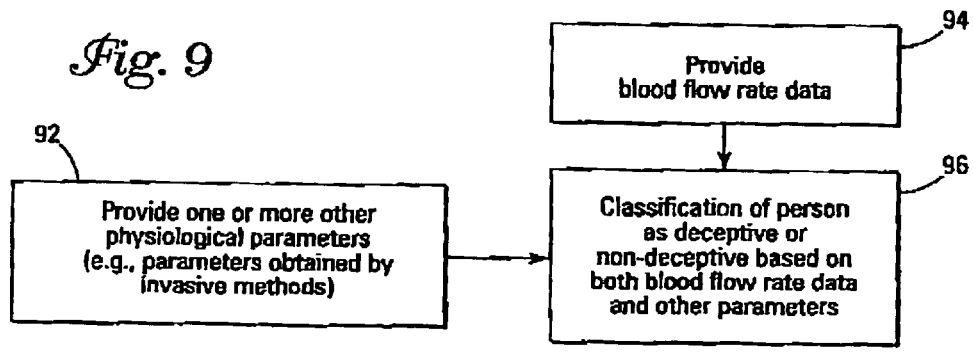

SYSTEM AND METHOD USING THERMAL IMAGE ANALYSIS AND SLOPE THRESHOLD CLASSIFICATION FOR POLYGRAPH TESTING

CROSS-REFERENCE TO RELATED APPLICATIONS

This application claims the benefit of U.S. Provisional Application No. 60/285,004, entitled "SYSTEM AND METHOD USING THERMAL IMAGE ANALYSIS FOR POLYGRAPH TESTING," filed Apr. 19, 2001, wherein such document is incorporated herein by reference.

GOVERNMENT RIGHTS

This invention was made with United States Government support under Contract No. DABT60-00-1-1003 awarded by the Agency: DoD Polygraph Institute. The United States Government has certain rights in this invention.

BACKGROUND OF THE INVENTION

The present invention relates generally to thermal analysis systems and methods. More particularly, the present invention pertains to polygraph testing of individuals.

Polygraph testing is a standard security procedure favored by various entities, e.g., governmental bodies, the military, etc. The objective of polygraph testing is to ascertain if the subject under investigation truthfully or deceitfully answers the questions presented thereto. Specially trained psychologists structure the questions to maximize elicitation.

Generally, during the testing, three physiological parameters are closely monitored. Such physiological parameters include blood flow rate, breathing rate, and perspiration rate. Typically, such physiological parameters are recorded using invasive methods and produce scalar values over time, e.g., signals. Then, a scoring system is used to quantify the subject's response and classify the subject's response as deceitful or truthful, i.e., deceptive or non-deceptive.

The success rate for conventional polygraph testing varies depending on the circumstances and persons being questioned. In some circumstances, the success rate may be very high, while in others, the success rate may be much lower. For example, when such polygraph tests are administered experimentally on the basis of a mock crime scenario, e.g., persons are questioned about a mock crime they supposedly perpetrated, the success rate is much lower.

There is generally a need for improved accuracy in such polygraph testing. This is particularly true in view of recent espionage cases. Improved accuracy will also promote the admissibility of polygraph testing in a general court system and potentially open new markets for use of such testing. Further, to use such testing, it must be simple to administer.

SUMMARY OF THE INVENTION

As such, according to the present invention, thermal image analysis methods and systems have been developed that address the needs described above. For example, the present invention may be used to provide true or pseudo, two-dimensional information (e.g., blood flow rate information across a significant portion of a person's face) as opposed to the one-dimensional information provided by traditional polygraph information channels (e.g., average blood flow rate at a particular point on a person, such as a person's wrist). With such information, accuracy can be improved.

Further, for example, the present invention provides for polygraph testing in a non-invasive manner, and therefore, simplifies the administration of the test.

The present invention may screen the entire facial area or use just one or more regions of the facial area of the subject to obtain thermal image data and, thereafter, process such data to obtain polygraph testing data. The thermal image data is transformed to blood flow rate data, e.g., the change in blood flow rate over time (or in other words over a plurality of frames of thermal image data).

Some embodiments of the methods according to the present invention include one or more of the following: providing thermal image data of at least a region of a face of a person; transforming the thermal image data to blood flow rate data; determining whether a person is deceptive based on blood flow rate data; classifying a person as deceptive or non-deceptive based on a change of blood flow rate over time in at least one region of the face of a person; classifying a person as deceptive or non-deceptive by generating a slope threshold representative of a demarcation between change of blood flow rate over time for a deceptive person and change of blood flow rate over time for a non-deceptive person; comparing a slope representative of change of blood flow rate over time for a person to a slope threshold to determine whether the person should be classified as deceptive or non-deceptive; providing thermal image data of at least a region proximate an eye of a person or of more than one region of the face of a person; acquiring thermal image data by asking a person a question to elicit a response therefrom, focusing a thermal infrared image device thereon, and capturing thermal image data during at least the response from the person; and determining whether a person is deceptive with respect to a response to a question.

Some embodiments of a system for use in detecting deception of a person include one or more of the following features: a thermal infrared image device operable to provide thermal image data of at least a region of a face of a person; a computing apparatus operable upon thermal image data to transform the thermal image data to blood flow rate data; a computing apparatus operable to determine whether a person is deceptive based on blood flow rate data; a computing apparatus operable to classify a person as deceptive or non-deceptive based on change of blood flow rate over time in at least one region of the face of a person; a computing apparatus operable to generate a slope threshold representative of a demarcation between change of blood flow rate over time for a deceptive person and change of blood flow rate over time for a non-deceptive person; comparing a slope representative of change of blood flow rate over time for a person to a slope threshold to determine if the person is deceptive or non-deceptive; a thermal infrared image device operable to provide thermal image data of at least a region proximate an eye of a person or one or more regions of the face of a person; a thermal infrared image device operable to capture a thermal image data during at least a period of time during an elicited response from a person; a computing apparatus operable to determine whether a person is deceptive based on blood flow rate data with respect to an elicited response; and a thermal infrared image device operable to capture frames of thermal image data during at least a period of time, and a computing apparatus operable to track movement of at least a region of a person's face during such time.

Another method according to the present invention for use in determining a physiological state of a person is described. The method includes providing thermal image data of at least a region of a face of a person and transforming the thermal image data to blood flow rate data. The blood flow rate data includes a slope representative of change of blood flow rate over time. Further, a slope threshold representative of a demarcation between change of blood flow rate over time for a first physiological state of a person and change of blood flow rate over time for a second physiological state of a person is provided. The slope representative of change of blood flow rate over time is compared to the slope threshold to determine whether the person is in the first or second physiological state, e.g., a deceptive state and a non-deceptive state.

Yet further, a system for use in determining a physiological state of a person is also described. The system includes a thermal infrared image device operable to provide thermal image data of at least a region of a face of a person and a computing apparatus. The computing apparatus is operable to transform the thermal image data to blood flow rate data. The blood flow rate data includes a slope representative of change of blood flow rate over time. The computing apparatus is further operable to provide a slope threshold representative of a demarcation between change of blood flow rate over time for a first physiological state of a person and change of blood flow rate over time for a second physiological state of a person, and yet further operable to compare the slope representative of change of blood flow rate over time to the slope threshold to determine whether the person is in the first or second physiological state, e.g., a deceptive state and a non-deceptive state.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE EMBODIMENTS

FIG. 2 is a graph of the electromagnetic (EM) spectrum.

FIG. 7 is one illustrative exemplary embodiment of thermal image acquisition shown generally in FIG. 4 according to the present invention.

FIG. 8 is one illustrative block diagram of a classification method according to the present invention using physiological parameters different than, and in addition to, blood flow rate data obtained using thermal image data.

FIG. 9 shows another illustrative block diagram of a classification method using one or more other physiological parameters other than, and in addition to, blood flow rate data obtained using thermal image data according to the present invention.

DESCRIPTION OF THE EMBODIMENTS

Figure 1:
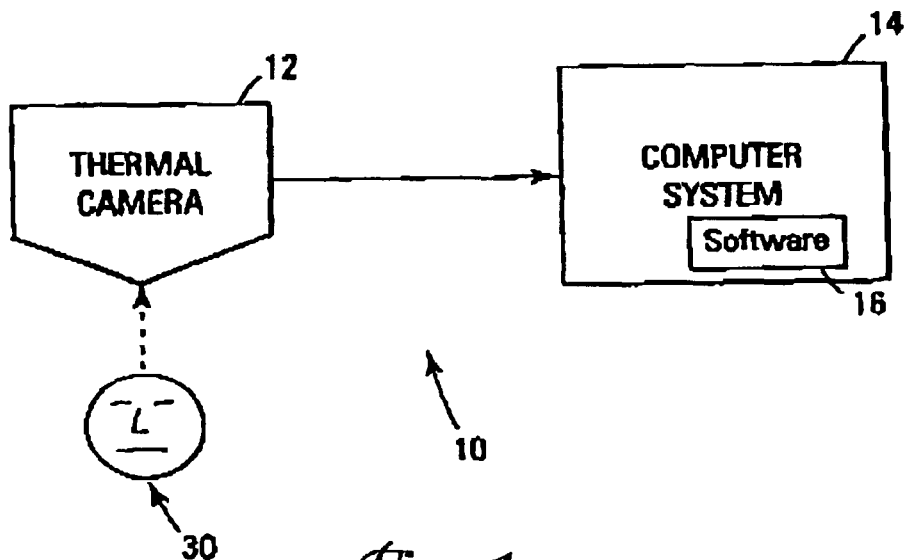
FIG. 1 is a block diagram illustrating one exemplary embodiment of a polygraph system according to the present invention.

The present invention shall be described with reference to FIGS. 1–11. Thereafter, an example of the present invention shall be described with reference to at least FIG. 12.

Generally, the present invention provides methods and systems for polygraph testing using thermal image analysis. The method generally includes the acquisition of thermal image data during at least a part of an interrogation session of a person (e.g., question and answer time periods), physiological correlation between such thermal image data and blood flow rate, and classification based thereon.

For example, facial thermal imagery using a mid-infrared camera may be performed. Thereafter, the raw thermal image data may be transformed to blood flow rate data through thermodynamic modeling. Finally, classifying a person as deceptive or non-deceptive may be performed based on one or more different classification processes, e.g., analysis of the blood flow rate data.

In other words, the present invention extracts subtle facial temperature fluctuation patterns through nonlinear thermodynamic modeling. The modeling transforms raw thermal image data to blood flow rate information. Such blood flow rate data can then be used as a feature of a binary classification scheme or any other classification scheme that will lead to beneficial determination of deception versus non-deception.

The methods and/or systems described herein which involve the use of thermal image data may be used alone in determining the deceptive or non-deceptive state of a person during questioning, or such methods and/or systems may be used in conjunction with other traditional polygraph testing methods. In other words, the thermal image analysis described herein may play a role in polygraph testing as an additional scoring channel in a traditional polygraph testing situation. Such an additional scoring channel may increase the accuracy and reliability of polygraph testing through the fusion of the non-invasive physiological measurements described herein using thermal image data with traditional invasive physiological measurements.

One or more of the illustrative embodiments of the methods and systems described herein provide one or more advantages. For example, the present invention includes a non-invasive polygraph testing process. As such, the person subjected to such polygraph testing is able to feel as comfortable as possible.

Further, for example, after appropriate processing of the thermal imagery according to one or more embodiments of the present invention, similar information to that achieved via conventional polygraph channels can be attained, i.e., blood flow rate data. In various embodiments, different types of information can be obtained. For example, at least in one embodiment described herein, such information includes pseudo two-dimensional blood flow rate information which may include average blood flow rate information taken over one or more regions of a person's face (in other words, for example, an average over a region greater than a point of a person's face). Further, true two-dimensional blood flow rate information may be attained which may include blood flow rate data at multiple points in one or more regions of the person's face. Of course, as described further below, tracking algorithms are required to obtain accurate point information. Such types of information are different and provide more accurate polygraph results than one-dimensional information which is obtained across the timeline in traditional or conventional polygraph testing, e.g., blood flow rate obtained using measurements at a point on the wrist of a person.

In U.S. patent application Ser. No. 09/776,470, filed Feb. 2, 2001, entitled "Detection System and Method Using Thermal Image Analysis," methods and systems for detecting anxiety through thermal facial image analysis are described. In general, the change in thermal facial image signature of an individual is used to determine whether the individual is experiencing anxiety. For example, as described therein, anxiety is accompanied by an increased local warming around the individual's eyes. This change in facial thermal pattern around the individual's eyes is typically accompanied by a concomitant cooling over the cheeks and/or concomitant warming over the carotid artery region.

Generally, this pattern of thermal change in an individual's body during an onset of anxiety (e.g., the change in the individual's thermal signature during onset of anxiety) makes physiological and evolutionary sense, as it represents a mechanism to facilitate rapid eye movement during preparedness for flight. In other words, elevated anxiety precipitates a host of physiological responses, many of which result from altered sympathetic nervous system activity. One of these responses is local redistribution of blood flow resulting in abrupt changes in local temperatures at various regions in the individual. Such changes in local temperatures in such regions are readily apparent in the human face where the layer of flesh over bone is relatively thin.

Such abrupt temperature changes in localized regions can be detected by human face emissions in both the mid-infrared thermal band (i.e., 3 microns to 5 microns band) and far-infrared thermal band (i.e., 8 microns to 14 microns band) of the electromagnetic spectrum. As one skilled in the art will recognize, such ranges may be slightly shorter or longer.

A graph of the electromagnetic spectrum is shown in FIG. 2, with the thermal infrared band shown as reference numeral 23. The thermal infrared band lies above the visible band 22 and reflected infrared band 21 of the electromagnetic spectrum.

As such, thermal infrared detectors suitable to sense temperature variations in such regions of the spectrum can be used to produce thermal facial images, or thermograms, representative of such local temperature changes in the human face of an individual. Such data of the thermograms (e.g., those using either one or more of the mid-infrared band and far-infrared band) may be used to determine a physiological state of the individual (e.g., anxiety), as described in U.S. patent application Ser. No. 09/776,470, which is incorporated herein by reference.

For example, as described in U.S. patent application Ser. No. 09/776,470, and as described herein with reference to FIG. 3, a thermal facial image of an individual 30 with reference to various regions of the individual's face 32 provide an individual signature that can be detected as anxiety. For example, as described above, an onset of anxiety in the individual 30 (e.g., such as that which may be induced by a startling stimulus, induced by fear when smuggling goods into a country, induced by fear arising from the need to establish an escape route when proceeding with covert operations in a secret area, etc.) is associated with a warming due to increased blood flow in the periorbital region 34 around the eyes 35 of the individual 30. The periorbital region size varies with the individual 30. This extra blood flow to the eye musculature in the periorbital region 34 is primarily redirected from the cheek regions with a corresponding cooling indicated therein.

With the above changes in temperature in the localized regions of the individual's face 32 that accompany an onset of anxiety, and with suitable monitoring of emissions from the individual 30 in the thermal infrared spectrum from before the time of anxiety onset (e.g., a thermal history) and also after the time of onset, detection of transition from a prior state, e.g., a calm state, to an anxiety state can be achieved. This change in facial thermal infrared pattern or signature at the time of the transition is dramatic and can be easily recognized as described in U.S. patent application Ser. No. 09/776,470.

However, in a polygraph test setting, when thermal image data is obtained, temperature changes observed around the eyes and in the face in general are typically only subtle and not abrupt as described in the onset of anxiety with reference to U.S. patent application Ser. No. 09/776,470. As such, when viewing only thermal image data as illustrated further below, such temperature changes are almost unnoticeable. Such disparity between the thermal image data changes due to anxiety and those due to polygraph testing are likely a result of the only subtle stress imposed on polygraph subjects.

Figure 5A:
FIGS. 5A–5B and FIGS. 6A–6B illustrate a comparison between thermal image data and thermal image data transformed to blood flow rate data according to the present invention.
Figure 5B:

Such unnoticeable temperature changes in the thermal image data obtained during polygraph testing is shown generally in FIGS. 5A–5B. FIG. 5A shows thermal image data of a person prior to and at the is beginning of responding deceptively to a question in a polygraph test. The temperature is visualized in gray scale, although any visualization scheme could be used, e.g., rainbow coloring scheme with higher temperatures represented by bright colors such as yellow and lower temperatures represented by other colors such as blue. FIG. 5B shows visualized thermal image data of a person towards the end of the person's deceptive response to the question. As can be seen in FIGS. 5A–5B, no noticeable difference in thermal image data appears.

Figure 6A:
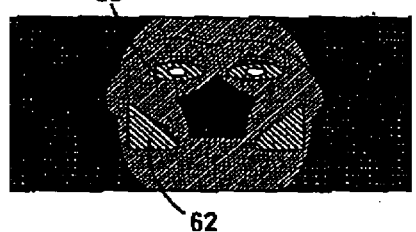
Figure 6B:
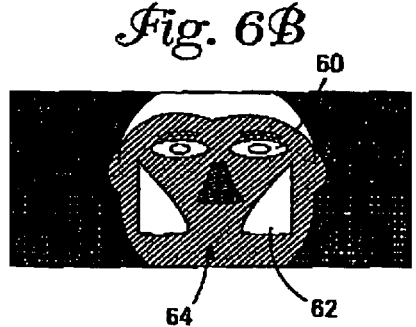

As such, to provide for useful information according to the present invention for use in polygraph testing, the thermal image data is transformed to blood flow rate data as described further herein and as visualized in FIGS. 6A–6B. In FIG. 6A, corresponding to the thermal image data of FIG. 5A, visualization of blood flow rate in a person prior to and at the beginning of a deceptive response to a question is shown generally as a very dark image. Lighter regions 60, 62 may be generally seen in the periorbital region 60 of the face and the cheek region 62 of the face. This is indicative of changing blood flow rate in such areas.

Towards the end of the person's deceptive response to the question, visualization of blood flow rate in the person's face corresponding to the thermal image data shown in FIG. 5B is provided in FIG. 6B. As shown in FIG. 6B, the change in blood flow rate in the periorbital region 60 is visualized as much lighter relative to that shown in FIG. 6A. Likewise, cheek region 62 is also visualized in a much lighter manner, as is a majority of facial skin 64, when compared to that of FIG. 6A.

The difference in the visualization of blood flow rate data between FIG. 6A and FIG. 6B is significant. The differences shown in the visualization of blood flow rate intensities are represented in such Figures with the lighter or brighter regions indicating the highest degree of change in blood flow rate. In other words, as the response to the question is answered deceptively, the change in blood flow rate from the time prior to the question to a time during the deceptive response is visualized in the Figures by the lighter representation of the face in FIG. 6B versus that shown in FIG. 6A.

Such differences between FIG. 6A and FIG. 6B are in direct contrast to the lack of differences in the visualized raw thermal image data shown for such individuals in FIGS. 5A–5B. As a result, according to the present invention, with amplification of the thermal image data (e.g., transformation of such thermal image data to change in blood flow rate over time), determination of whether a person's response to a question is deceptive or non-deceptive can be attained.

In view of the preceding generalities, an illustrative embodiment of a polygraph system 10 according to the present invention shall be described with reference to FIG. 1. In conjunction with this polygraph system 10, preferably, various software routines or algorithms 16 are generally described for carrying out various steps of one or more embodiments of a polygraph method (e.g., polygraph method 50 shown in FIG. 4) for determining whether response by an individual (e.g., a statement by an individual) is deceptive or non-deceptive (e.g., whether a person is being deceitful or truthful).

The polygraph system 10, e.g., a system for determining whether an elicited response from a person 30 is deceptive or non-deceptive, is generally illustrated in FIG. 1. The polygraph system 10 includes a thermal infrared image device 12 operable to provide suitable thermal image data representative of a scene in which individual 30 (see also FIG. 3) is located. The thermal image data from the thermal infrared image device 12 is provided to a computing apparatus 14.

Preferably, computing apparatus 14 includes a computer system operable to execute software 16 to provide for the determination of the deceptive or non-deceptive state of a person based on thermal image data transformed to blood flow rate data. Although the computing apparatus 14 may be implemented using software 16 executable using a processor apparatus, other specialized hardware may also provide the functionality required to provide a user with information as to the non-deceptive or deceptive state of an individual 30. As such, the term computing apparatus as used herein includes specialized hardware in addition to or as an alternative to a processor apparatus capable of executing various software routines.

The computing apparatus, which shall be referred to hereinafter in conjunction with reference numeral 14, may be, for example, any fixed or mobile computer system, e.g., a personal computer. The exact configuration of the computer system is not limiting and most any device capable of providing suitable computing capabilities may be used according to the present invention. Further, various peripheral devices, such as a computer display, a mouse, a keyboard, a printer, etc., are contemplated to be used in combination with a processor in the computing apparatus 14.

The thermal infrared image device 12 is preferably one or more thermal cameras having a pixel array sensitive to the mid-infrared and/or far-infrared bands of the electromagnetic spectrum. For example, the thermal infrared image device 12 may be an uncooled thermal camera sensitive in the far-infrared band (i.e., the 8 micron to 14 micron band) available from Raytheon and provided under the trade designation Explorl R. Further, for example, the thermal infrared image device 12 may be a mid-infrared camera sensitive in the mid-infrared band (i.e., the 3 micron to 5 micron band) available from Raytheon under the trade designation Radiance HS Mid-Infrared Camera.

As indicated previously, the human body and face emit in both the mid-infrared and far-infrared bands of the electromagnetic spectrum. Therefore, preferably, both a far-infrared camera and a mid-infrared camera are used to provide thermal image data such that the data in the far-infrared band and the mid-infrared band may be compared to provide additional accuracy. However, one skilled in the art will recognize that either one or both of a far-infrared band and/or mid-infrared band camera may be used according to the present invention. Further, it is preferred that highly sensitive cameras be used when attempting to detect subtle changes in physiological response.

The far-infrared camera provided under the trade designation ExplorlR has a nominal temperature sensitivity of noise equivalent temperature difference (NETD) equal to 0.15° C. However, such performance is typically not obtained and the actual temperature sensitivity of the ExplorlR model may be above 0.5° C. As this is only a fair amount of facial temperature resolution, a certain amount of information may be masked thereby. The mid-infrared camera available from Raytheon under the trade designation Radiance HS Mid-infrared Camera may be calibrated for a particular setting with nonlinear equations for improved accuracy. It generally has an NETD equal to 0.025° C. A calibration process may be complemented with a smart, highly accurate (0.01° C.) differential black body for near perfect scene temperature reference.

The computer apparatus 14 includes software components 16 for operation on thermal facial image data provided from thermal infrared camera 12. One or more of such software components 16 may be used to operate on the thermal image data, e.g., pixel data, provided from the thermal infrared camera 12 to determine whether an individual 30 is non-deceptive or deceptive with respect to an elicited response therefrom. Such algorithmic software components for analysis of the thermofacial images of an individual 30 are shown as a part of an exemplary flow or block diagram of the polygraph method 50 shown in FIG. 4.

Figure 4:
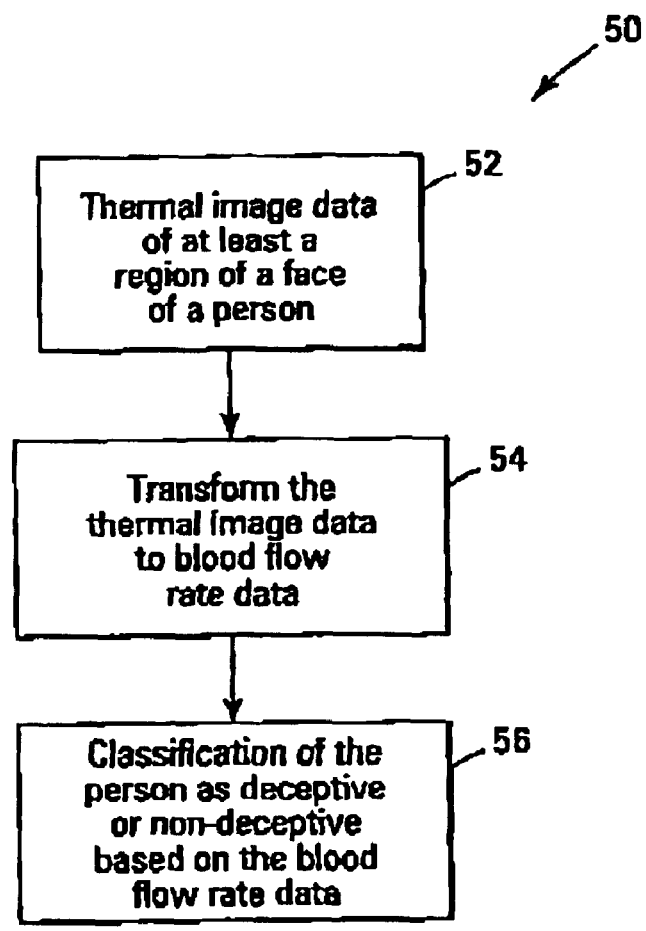
FIG. 4 is a general block diagram illustrating one exemplary embodiment of a polygraph method according to the present invention.

As shown in the polygraph method 50 of FIG. 4, thermal image data 52, e.g., pixel data, of a scene in which the individual 30 is located is provided to the computer apparatus 14 and is thereafter operated upon by software 16. Such software 16 includes at least a transformation component (block 54) for transforming the captured thermal image data for a person to blood flow rate data and a classification component (block 56) for classifying the person as deceptive or non-deceptive based on the blood flow rate data.

Generally, transformation component 54 provides an algorithm to transform thermal image data of the face 32 of an individual 30 to blood flow rate information (e.g., blood flow rate, change in blood flow rate over time, etc.) embodied as blood flow data. Preferably, such transformation changes the thermal image data into data representative of the change of blood flow rate over time (i.e., over a plurality of frames) of one or more regions of the face.

Figure 3:
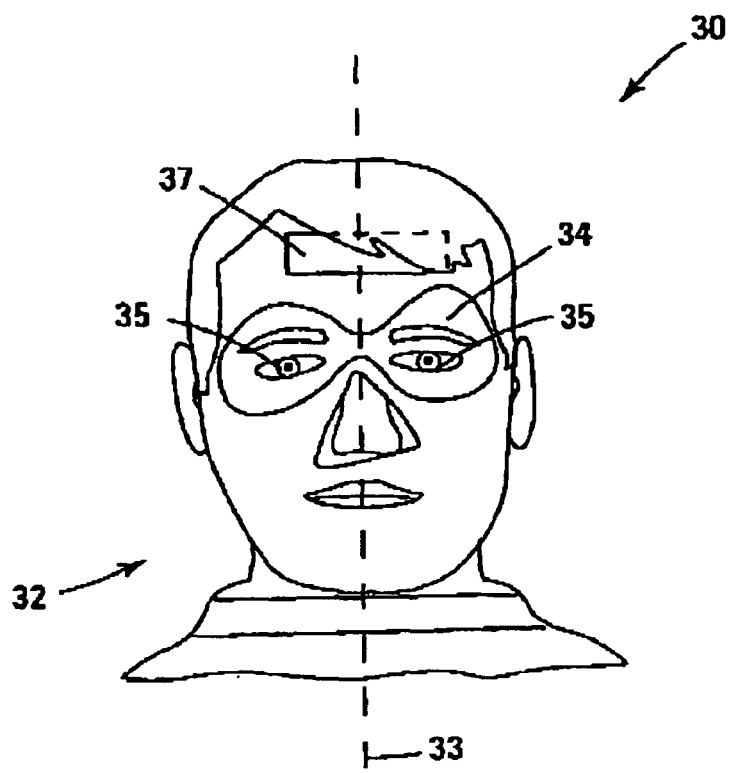
FIG. 3 is a diagram of an illustrative thermal facial image according to the present invention.

Such transformation may include any number of different processing techniques. For example, such transformation may include segmentation algorithms to separate thermal image data of the face from background of the thermal image data of the scene provided from camera 12. Likewise, a face partition component may provide the ability to partition the thermal image data of the face 32 into one or more regions. In one exemplary embodiment, as shown in FIG. 3 and as described elsewhere herein, the periorbital region 34 is preferably used according to the present invention.

It will be recognized by one skilled in the art that any number of regions may be used in the polygraph method described herein, e.g., the periorbital region, the cheek region, a forehead region, a nasal region, etc. However, certain regions may provide more beneficial information relative to the others. Further, as described elsewhere herein, blood flow rate for one or more points of one or more regions of the face (e.g., a network of points) may be used to provide true two-dimensional blood flow rate data for polygraph testing.

Further, generally, the classification component (block 56) provides an algorithm operable upon the transformed thermal image data to determine whether an individual 30 is being deceptive or non-deceptive. For example, automatic classification of the individual 30 into a deceptive or non-deceptive classification may be performed. Such classification may be performed by one of various types of classification algorithms such as, for example, a pattern recognition algorithm that is a part of a class of algorithms using statistical learning methodology. Such algorithms, for example, may be used to correct for some variability in the thermal signatures across the human race. Further, for example, as further described herein, baseline and/or threshold based classification techniques may be used.

Therefore, generally, the polygraph method 50 as shown in FIG. 4 includes the provision of thermal image data of at least a region of the face of a person (block 52). The thermal image data of at least the region of the face of a person is transformed to blood flow rate data (block 54). Thereafter, the blood flow rate data is used for classification of the person as being deceptive or non-deceptive (block 56), for example, with respect to a response elicited from the person.

FIG. 7 is one illustrative embodiment of acquisition of thermal image data shown generally in block 52 of polygraph method 50 in FIG. 4. Generally, as shown in FIG. 7, a response from a person is elicited by asking the person a question (block 72). Thermal image data of at least a region of the face of the person asked the question is acquired during at least the response to the question (block 74) (e.g., thermal image data may be captured during the question, during the response, after the response, etc.). For example, thermal image data of at least a region of the face in a scene is received from a thermal infrared camera, e.g., thermal infrared image device 12 of FIG. 1. Such thermal image data includes pixel data of at least one frame of the scene. Preferably, however, a plurality of frames are provided from the thermal infrared camera.

The pixel information may be either in the form of digital values or direct temperature readings. Of course, the digital values are proportional to the actual scene temperatures at the respective points or pixels. In other words, pixel values have either indirect or direct correlation to scene temperatures. This is in contrast to visible band images, where pixel values have direct correlation to reflectance values.

Such received thermal image data representative of the thermal characteristics of a scene may be directly displayed and/or stored by the computing apparatus 14. For example, software associated with computing apparatus 14 may allow for the direct display of such data in degrees centigrade. For example, in many commercial systems, such data may be provided in grayscale values. Such grayscale display of images may generally have a poor visualization affect. Other commonly employed rainbow or pseudo-coloring display schemes may have relatively better imaging quality but achieve optimal results for the dynamic range of the visible band of the electromagnetic spectrum. Although such methods of display may be used, it is noted that visualization of the thermal image data prior to transformation provides little, if any, beneficial information in the determination of deceptiveness.

Optionally, at least the face of a person, e.g., the human head, can be tracked in the scene as it moves around during the length of polygraph testing as the thermal image data is being acquired. Such tracking is preferable, as an accurate solution of the differential thermodynamic equation for transforming thermal image data to blood flow rate data operates point-wise and across frames. However, although tracking provides for a more accurate determination of deceptive versus non-deceptive behavior by the person, the present invention may be performed assuming a completely stationary subject for short periods of time.

With a face tracking algorithm in place, a network of points of the face can be developed where blood flow rate can be monitored over time. This is true two-dimensional information as opposed to pseudo two-dimensional information, e.g., average blood flow over a region of pixels. However, averaging blood flow rate in the periorbital area, or over a substantial facial area is tolerant to registration errors and is a practical alternative to use of a head tracking algorithm and/or the use of a network of points process.

Thermal image data may be acquired for one region of the face, e.g., periorbital region 34 of an individual 30, as shown in FIG. 3, or may be acquired for a plurality of regions. As indicated above, blood flow rate over a substantial facial area may be more tolerant to registration errors.

The thermal image data of the scene may be operated upon by a segmentation algorithm as previously mentioned to separate a person's face from background of the scene captured. For example, the segmentation process may compare thermal image data from at least one region of the scene to thermal image data of another region of the scene. As the thermal characteristics of the human face are usually well contrasted to those of the background, such comparison and segmentation can be easily implemented. The comparison results in data which can be used to separate the human face from the background. The thermal image data of the human face separated from the background can then be used in later processes, e.g., by a transformation component (block 54 in the polygraph method 50 of FIG. 4).

Further, partitioning of the face may also be provided by comparing thermal image data of one region to thermal image data of another region to distinguish particular regions from each other. For example, the underlying anatomical features of the face 32 facilitate orientating the face 32 for partitioning.

For example, as shown in FIG. 3, the face 32 is bilaterally symmetrical about plane 33 (defined through the face 32, e.g., orthogonal to the FIG. 3) and aids partitioning into regions of interest, e.g., one eye in each half of the face, the nose lying half on one side of the plane 33 and half on the other side of the plane 33, etc. As such, generally, there is also symmetry of thermal image data from one side of the face to the other side.

One can achieve demarcation or partitioning of the facial regions using various algorithm methods. For example, a region competition algorithm derived by minimizing the generalized Bayes/MDL criterion using variational principle may be used for such demarcation of the facial regions. Such algorithms are described in an article by S. C. Zhu and A. Yuille, entitled "Region Competition: Unifying Snakes, Region Growing, and Bayes/MDL for Multiband Image Segmentation," IEEE Transactions on Image Analysis and Machine Intelligence, Vol. 18, No. 9 (September 1996).

Preferably, the segmentation and partitioning algorithms should be able to perform on static images as well as on dynamic sequences of images, e.g., video clips, live video feeds, etc. As such, in the case of image sequences, e.g., dynamic image sequences provided in a real-time fashion, a thermal statistic/tracking and update component may be used to lock onto the face and/or one or more of the segmented or partitioned regions of interest. Such segments or regions of interest may then be tracked from frame to frame with the particular thermal image data noticed or identified immediately. Further, data from multiple images may be used to provide accurate and effective thermal image data of one or more regions of interest. The thermal image data of one or more of the regions of interest, e.g., the periorbital region, the cheek region, etc., provide information that can be used for classification by the classification component (block 56 as shown in the polygraph method of FIG. 4).

In other words, thermal image data acquisition block 52 may be used to continuously lock onto the face and the segmented or partitioned regions of interest therein from frame to frame throughout a period of time. The thermal image data of one or more of the regions obtained throughout this dynamic tracking can be updated dynamically from frame to frame to provide the necessary thermal image data for use according to the present invention. The various processes described above, e.g., segmentation, partitioning, etc., either together or one or more thereof, may operate as preprocessing routines to provide thermal image data for transformation thereof to blood flow rate data. Such blood flow rate data may then be used for classification (block 56).

One skilled in the art will recognize that various preprocessing routines may be performed with respect to the thermal image data prior to providing such thermal image data for transformation to blood flow rate data and that the present invention is not limited to only those briefly described herein.

The transformed blood flow rate data based on the thermal image data may be used alone (i.e., as a sole physiological parameter) for classification of a person as deceptive or non-deceptive with respect to an elicited response therefrom (classification block 56 in the polygraph method 50 shown in FIG. 4). However, such transformed blood flow rate data may also be used in combination with one or more other physiological parameters different than blood flow rate data obtained using thermal image data as shown and described with reference to FIGS. 8 and 9.

FIG. 8 provides for classification of a person's elicited response as non-deceptive or deceptive based on blood flow rate data as shown by block 86. For example, such classification may be the result of the polygraph method 50 as shown in FIG. 4. In addition, a classification of the person's elicited response as deceptive or non-deceptive is also provided based on other physiological parameters (block 84).

For example, polygraph testing is a standard procedure that conventionally has used one or more physiological parameters to determine whether a person's answers to questions are deceptive or non-deceptive, i.e., deceitful or truthful. During such conventional polygraph testing, physiological parameters such as blood volume and pulse change, respiratory changes, and electro-dermal activity have been recorded using invasive techniques and are then used for determining truthfulness of a person. The present invention as shown in FIG. 8 uses one or more of such other physiological parameters, i.e., physiological parameters obtained by invasive methods that are different from blood flow rate data obtained according to the present invention using thermal image data, to classify an individual as deceptive or non-deceptive. For example, as shown in FIG. 8, such other physiological parameters are provided as shown in block 82 and the classification is performed based on such parameters in block 84.

Thereafter, the classification of whether the person is being deceptive or non-deceptive based on blood flow rate data obtained using thermal image data (block 86) may be used to confirm the classification of an individual based on one or more other physiological parameters provided to the process (block 82 and block 84). Likewise, the classification based on blood flow rate data obtained using thermal image data (block 86) may be confirmed using a classification resulting from the measurement of the other physiological parameters different than blood flow rate data obtained using thermal image data (blocks 82 and 84).

Also, as shown in FIG. 9, both blood flow rate data (block 94) and one or more other physiological parameters different than blood flow rate data obtained using thermal image data (block 92) may be provided to a classification algorithm. Classification of a person as deceptive or non-deceptive may be based on both the blood flow rate data obtained using thermal image data and the one or more other physiological parameters, e.g., parameters obtained by invasive methods. For example, an algorithm taking both data gathered non-invasively and data gathered invasively into consideration when arriving at a classification may be used.

One skilled in the art will recognize that classification based on blood flow rate data obtained using thermal image data may be used for any other purpose in polygraph testing. For example, confirmation of other classifications, use in classifying individuals, preliminary determinations of deception or non-deception may be used to invoke other applicable polygraph testing methods or steps, etc.

Further, blood flow rate data determined according to the present invention may be used for other beneficial purposes other than polygraph testing. For example, monitoring of the blood flow rate data determined according to the present invention may be used for a particular medical application, e.g., control of a process or apparatus based on the monitored data. In other words, the transformation of thermal image data to blood flow rate data according to the present invention is a unique manner of attaining blood flow rate information to be used in other types of processes or apparatus.

Further, just as described in U.S. patent application Ser. No. 09/776,470, the present invention may be used to detect other physiological states of a person through the analysis of the thermal image data including the transformation to blood flow rate data. For example, in addition to deceptive versus non-deceptive determinations, the methods and systems described herein may be used to determine one or more different physiological states of a person, e.g., depression, periods of dementia, anxiety, etc. The term anxiety as used herein generally identifies a set of feelings. This set of feelings may include one or more of alertness, anxiety, fear, and the like. Such a set of feelings are generally symptomatic in individuals at the time individuals are engaged in certain activities, such as deception, terrorist or illegal activities. Such feelings or symptoms are produced by the sympathetic system and cannot be totally controlled by the person. As such, they provide a biometric indicator, e.g., measurable physiological response, that is extremely difficult to conceal.

Figure 10:
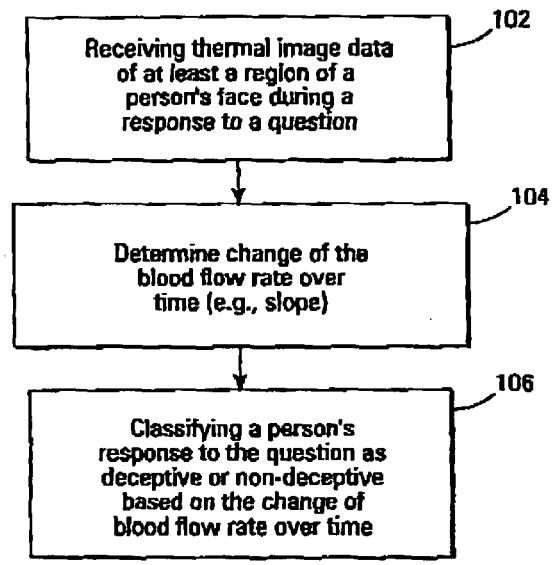
FIG. 10 shows an exemplary embodiment of a thermal image data transformation process and classification process generally shown in the method of FIG. 4.

FIG. 10 shows one exemplary embodiment of a flow diagram for transformation component (block 54) in combination with classification component 56 (block 56) of the polygraph method 50 shown in FIG. 4. As shown by block 102, thermal image data acquired via the thermal image acquisition component 52 of polygraph method 50, as shown in FIG. 4, is received for at least a region of a person's face during at least an elicited response to a question. Such thermal image data has been described previously herein.

Thereafter, change of the blood flow rate over time (e.g., slope) is then determined based on the thermal image data (block 104). In other words, slope representative of the change of blood flow rate over time for thermal image data received from the thermal infrared image device (e.g., device 12 of the polygraph system 10 of FIG. 1) is determined.

Such blood flow rate change over time can be determined from the thermal image data as described below. The fluctuation of temperature in the various facial areas is primarily due to the changing blood flow rate.

Thermodynamic modeling shows that the blood flow rate is inversely proportional to the square of the skin temperature deviation from the temperature at the core of the human body. This nonlinear relation amplifies the weak temperature change patterns observed in polygraphy subjects and brings the information noise down to levels such as that described in the anxiety determination application, U.S. patent application Ser. No. 09/776,470.

Specifically, at thermal equilibrium, one can model the heat balance equation for human skin tissue as:

$$Q_r + Q_e + Q_f = Q_c + Q_m + Q_b,$$

where $Q_r$=the heat radiated from the subject to the air in units of calories;

$Q_e$=the basic evaporated heat;

$Q_f$=the heat loss via convention into the air neighboring the skin surface;

$Q_c$=the heat conducted by subcutaneous tissue;

$Q_m$=the heat corresponding to the metabolic rate of cutaneous tissue; and $Q_b$=the heat gain/loss via convection attributable to blood flow of subcutaneous blood vessels.

Observing skin temperature change ($\Delta T_s$) in a short period ($\Delta t$), the following equation results:

$$C_s \Delta T_s = -(\Delta Q_r + \Delta Q_e + \Delta Q_f) + (\Delta Q_c + \Delta Q_m + \Delta Q_b),$$

where $C_s$=the heat capacity of skin.

For short periods of time ($\Delta t$), and assuming that the subject did not recently have a sizeable meal, one can consider the term $\Delta Q_m$ as negligible. The terms $\Delta Q_r$, $\Delta Q_e$, and $\Delta Q_f$ are shown to be of magnitude approximately 1/100 less than the magnitude of $\Delta Q_b$. Therefore, $$C_s \Delta T_S \sim Q_c + \Delta Q_b$$

$$= \alpha p_c V_{S_2}(T_B - T_{S_2})$$

$$S - \alpha p_c V_{S_1}(T_B - T_{S_1})$$

$$S + K_c(T_B - T_{S_2})/(3d) -$$

$$K_c(T_B - T_{S_1})/(3d) = \alpha$$

$$p_c \Delta V_S T_B S - \alpha p_c$$

$$(V_{S_2} T_{S_2} - V_{S_1}$$

$$T_{S_1}) S - K_c \Delta T_S/(3d)$$

$$= \alpha p_c \Delta V_S T_B S - \alpha p_c$$

$$((V_{S_1} + \Delta V_S)(T_{S_1}$$

$$+ \Delta T_S) - V_{S_1} T_{S_1})$$

$$S - K_c \Delta T_S/(3d) = \alpha p_c$$

$$\Delta V_S T_B S - \alpha p_c \Delta V_S$$

$$T_{S_1} S - \alpha p_c V_{S_1} \Delta T_S$$

$$S - \alpha p_c \Delta V_S \Delta T_S S - K_c$$

$$\Delta T_S/(3d) = \alpha p_c \Delta V_S$$

$$(T_B - T_{S_2}) S - \alpha p_c V_{S_1}$$

$$\Delta T_S S - \alpha p_c \Delta V_S \Delta T_S$$

$$S - K_c \Delta T_S/(3d)$$

where $\alpha$=0.8 (countercurrent heat exchange in a warm condition);

Pc=0.92 cal/mUK (heat capacity of blood);

$V_{s_i}$: i=1,2=the skin blood flow rate at times $t_1$ and $t_2$;

$T_B$=310 K (blood temperature in the core);

$T_{s_i}$; i=1,2= the skin temperature at times $t_1$ and $t_2$;

S=the thickness of the skin;

$K_c$=0.168 kcal/m/h/K (thermal conductivity of skin); and d=the depth of core temperature point from skin surface.

After differentiating, the following equation is obtained:

$$C_S \frac{dT_S}{dt} \approx \alpha p_c \frac{dV_S}{dt}(T_B - T_S)S - \alpha p_c V_S \frac{dT_S}{dt} S - \alpha p_c \frac{dV_S}{dt}\frac{dT_S}{dt} S - K_c \frac{dT_S}{dt} \bigg/ (3d). \quad (3d).$$

Ignoring the term involving $$\frac{dV_S}{dt}\frac{dT_S}{dt},$$

one obtains the following equation:

$$\frac{dV_S}{dt} = \frac{T_B(C_S + K_c/(3d)) - C}{(T_B - T_S)^2}\frac{dT_S}{dt},$$

where C is a constant.

For calibrated thermal imagery, one can calculate the discrete-time approximation to the derivative of the temperature $$\frac{dT_S}{dt}$$

as the difference between a pair of images normalized by the number of sample frames between the respective acquisition times. The expression $T_B(C_S+K_c/(3d))-C$ represents a constant. Therefore, one can estimate the term $$\frac{dV_S}{dt},$$

except for an unknown scale factor. The expression for $$\frac{dV_S}{dt}$$

can be integrated numerically to obtain an estimate for $V_S$. To arrive at $$\frac{dV_S}{dt} = \frac{T_B(C_S + K_c/(3d)) - C}{(T_B - T_S)^2} \frac{dT_S}{dt},$$

one must consider the metabolic heat component as negligible.

By solving this equation for every pixel in the image, the raw thermal data can be transformed to blood flow rate data. To ensure a meaningful application of the equation, the image can be cropped so that it contains only the subject's face and no background, e.g., by segmentation, partitioning, etc. For example, cropping can be performed at the first frame of each video clip and cropping dimensions applied across the timeline to the end of a particular question-answer session. This assumes a stationary subject for the short duration (5–10 seconds) of the question-answer session. Based on experimental experience, the stationary subject assumption is valid, although some agitated subjects moving noticeably during such short periods of time may affect some determinations.

Figure 12:
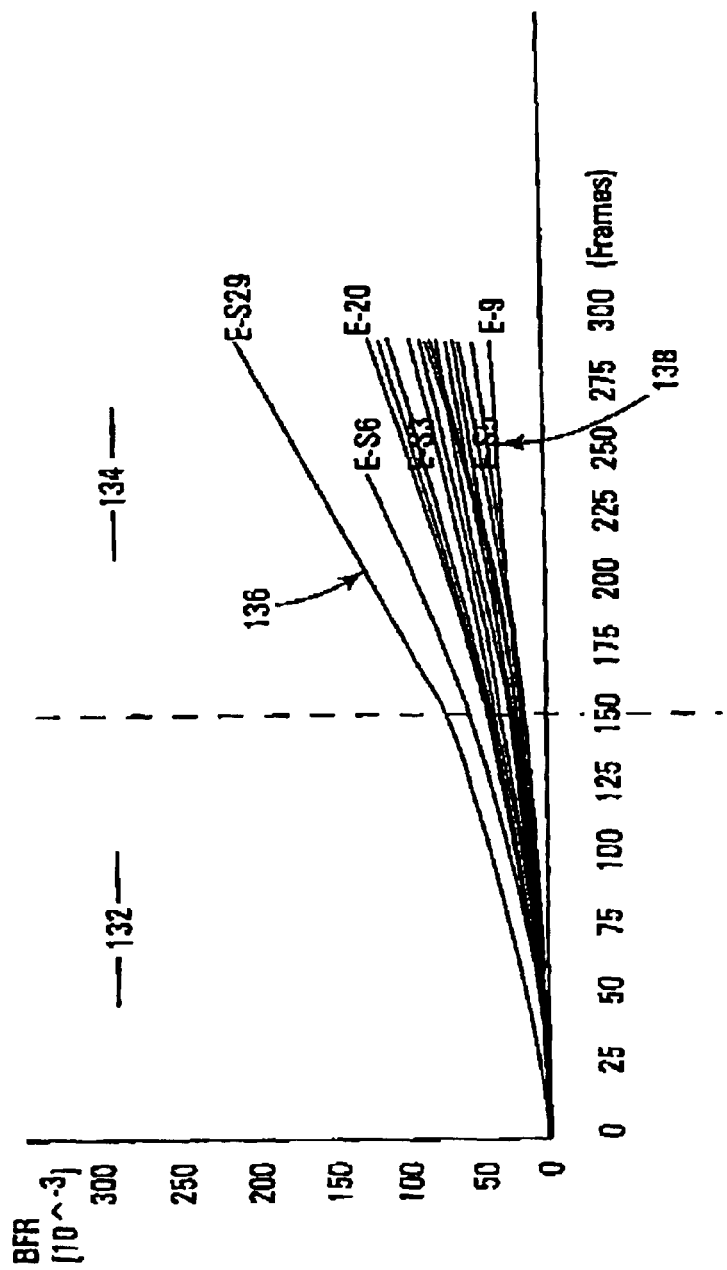
FIG. 12 is a graph for use in describing an illustrative example of a polygraph method and system according to the present invention.

In the embodiment of FIG. 10, the respective average blood flow rate for each frame is then determined and a signal is produced representative of average blood flow rate from frame to frame. Such a signal for which an example has been plotted in FIG. 12, provides blood flow rate over frames of thermal image data that can be used for classification purposes.

After transformation of the thermal image data to blood flow rate data (block 104), as shown in FIG. 10, such change of blood flow rate over time may be used to classify a person's response to the question as deceptive or non-deceptive based on the change of blood flow rate over time (block 106).

Classifying the person's response to the question as deceptive or non-deceptive based on the change of blood flow rate (block 106) may be performed via one or more different classification processes. Two specific classification processes are described with reference to FIGS. 11A–11B, wherein a slope threshold is generated. However, various other classification processes are possible.

For example, software associated with computer apparatus 14 may allow for the direct display or visualization of blood flow rate data in terms of the intensity of such blood flow rate data. For example, such data may be provided in grayscale values even though such grayscale display of images may generally have a poor visualization effect. Other commonly employed rainbow pseudo-color display schemes may provide relatively better visualization effects.

In other words, blood flow rate data may be directly displayed on a display screen and classification may be performed manually by the person viewing the blood flow rate data on the display. For example, as shown in FIGS. 6A–6B, a large difference in blood flow rate data is visually displayed. The user may manually classify the individual as being deceptive or non-deceptive based on the change of blood flow rate data viewed on the display. As such, classification software component (block 106) may be implemented through software that displays the blood flow rate data of the human face or a region thereof to a user, e.g., using a rainbow pseudo-coloring technique. However, preferably, other types of classification processes, e.g., automated, real-time systems, are preferred.

For example, pattern recognition/classification software may perform automatic classification. Preferably, such algorithms of the software operate in a training and performance mode. For example, in the training mode, the software component may include algorithms that belong to the class of statistical learning methodology such as described in M. I. Jordan and R. A. Jacobs, entitled "Hierarchical Mixtures of Experts and the EM Algorithm," Neural Computation, Vol. 6, pps. 181–214 (1994). In such a training mode, as the routine learns about the statistical blood flow rate data with regard to individuals in deceptive versus non-deceptive states, algorithms can be updated and the accuracy of such classifications will become more reliable. The performance mode of the algorithm operates to perform the actual classification.

Further, the classification process may use a comparison of blood flow rate data to a determined baseline to perform classification. The baseline reference may, for example, be a baseline of a deceptive versus a non-deceptive blood flow rate or signature of a deceptive person. For example, statistical analysis may be used to develop a baseline for an individual in a non-deceptive state versus a deceptive state. Various response variabilities across the human race may need to be considered.

In other words, the dependence of the non-deceptive state versus deceptive state may be shown by varied blood flow rate images depending on various factors. For example, the mental state of the individual, the intelligence of the individual, the race of an individual, the physical conditioning of an individual, the blood pressure of an individual, and many other variables across the human population will effect the blood flow rate data of an individual in a deceptive versus a non-deceptive situation.

In addition, other conditions relative to obtaining thermal image data from an individual must also be considered. For example, the effect of temperature and light on the scene may need to be considered.

As such, with a collection of experimental data and analysis thereof, a baseline reference covering a large population may be determined.

Once a baseline reference is set, e.g., such as for a particular region (e.g., periorbital region) of the face, then thermal image data may be acquired, transformed to blood flow rate data, and compared to the baseline reference. For example, thermal image data may be captured and transformed for a periorbital region of an individual. Thereafter, the blood flow rate data for the periorbital region can be compared to a threshold level determined from the baseline reference developed for an individual in a deceptive versus non-deceptive state.

Yet further, the blood flow rate data, or signals representative thereof, may be used as feature vectors in a nearest neighbor (NN) classifier setting such as that described in E. Gose et al., entitled, "Pattern Recognition and Image Analysis," pp. 159–186, Prentice-Hall, Upper Saddle River, N.J. (1993). Nearest in NN refers to the smallest Euclidean distance in 300-dimensional space, where 300 is the number of frames acquired. In such a process, the aim is to classify the majority of the subjects based on their distance from a small number of control subjects. The population of the control subjects should be unbiased.

Alternatively, one can establish the ideal blood flow rate signals for the deceptive and non-deceptive case and measure the respective Euclidean distances. These ideal deceptive and non-deceptive blood flow rate signals should correspond to the expected physiological response in stressful and non-stressful situations.

Figure 11A:
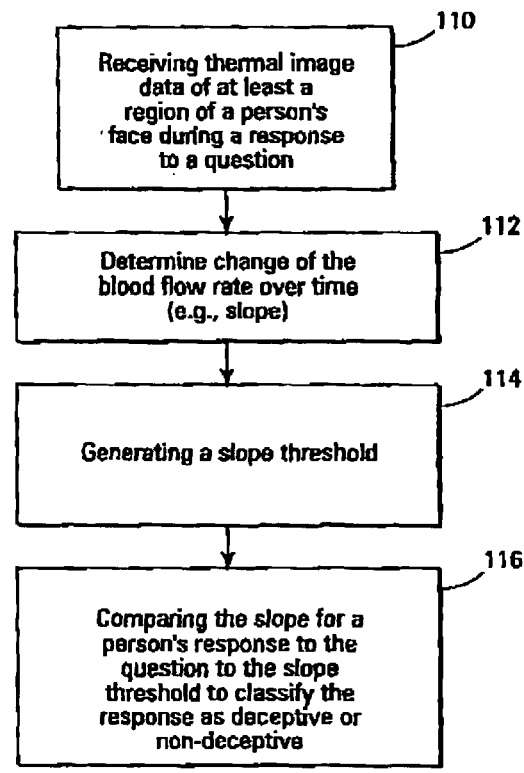
FIGS. 11A–11B show alternative flow diagrams of the transformation and classification processes shown generally in the polygraph method of FIG. 4 according to the present invention.

FIG. 11A shows one embodiment of a classification process based on a slope threshold generated using a thresholding algorithm applied to slope data of deceptive and non-deceptive change in blood flow rate over time. As shown in FIG. 11A, thermal image data is received for at least a region of a person's face during a response to a question (block 110). Thereafter, change of the blood flow rate over time is determined (block 112).

The slope threshold generated is based on slope data for a number of subjects, both non-deceptive and deceptive (block 114). Ideally, the slope data should form a bi-modal distribution; one for the non-deceptive subjects and one for the deceptive subjects. This classifier can be tested by feeding the slope data into a thresholding algorithm. For example, the slope data may be representative of the change of blood flow rate over time during responses of subjects (see, for example, region 134 in FIG. 12.)

One such thresholding algorithm that may be used is described in the article by N. Otsu, entitled "A Threshold Selection Method from Gray-Level Histograms," *IEEE Transactions on Systems, Man & Cybernetics*, Vol. 9, No. 1, pps. 62–65 (1979). This algorithm has reliable performance in bi-modal distributions. It involves a non-parametric and unsupervised method of threshold selection. An optimal threshold is selected in order to maximize the separability of the result in classes. The algorithm utilizes only the zeroth-order and first-order cumulative moments of the histogram.

Once the slope threshold is generated based on the slope data for a plurality of non-deceptive and deceptive subjects, then the slope threshold can be used to make binary decisions. Such binary decisions can be made by comparing the slope representative of the change of blood flow rate over time for a person responding to a question to the slope threshold so as to classify the person's response as deceptive or non-deceptive (block 116). For example, if the slope is smaller than the threshold, then one may classify the answer as a non-deceptive response, e.g., the subject being non-deceptive. Likewise, if the slope is larger than the slope threshold, then one can classify the elicited response or answer as deceptive.

Figure 11B:
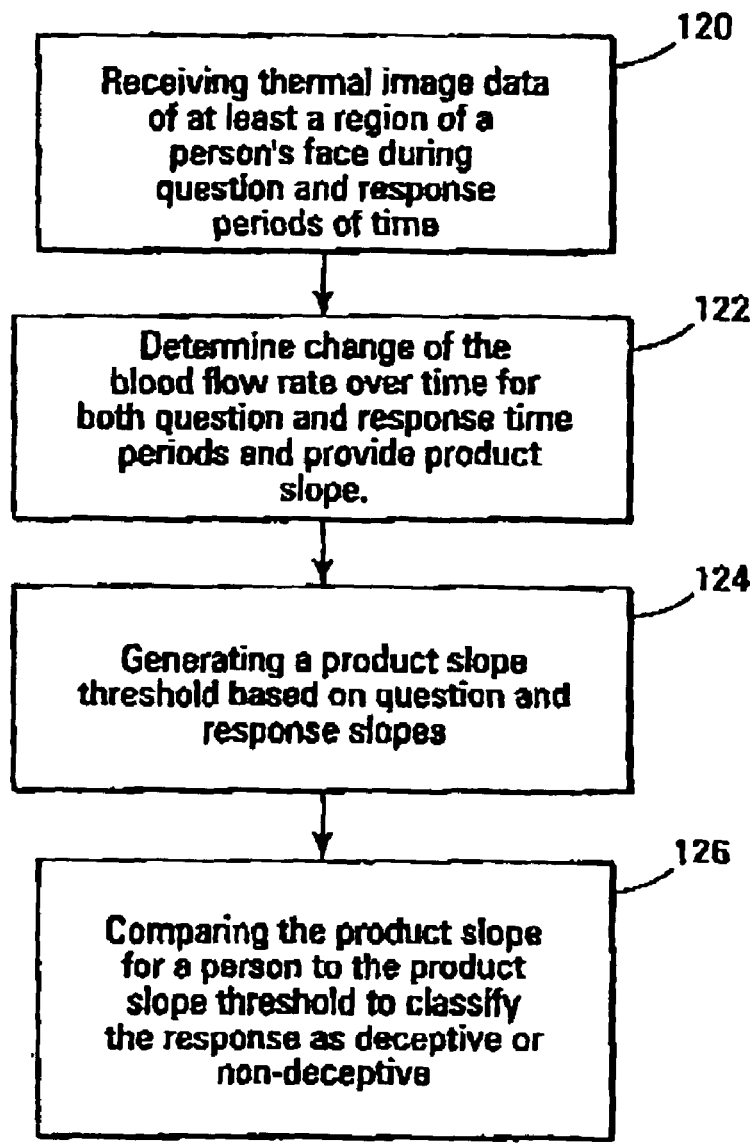

FIG. 11B shows a classification process that is substantially the same as the classification process described with reference to FIG. 11A, except that the slope threshold generated is a product slope threshold based on the product of the slope representative of the change of blood flow rate over time for a plurality of deceptive and non-deceptive persons during the question time period (see, for example, region 132 of FIG. 12) and the slope representative of the change of blood flow rate over time for a plurality of deceptive and non-deceptive persons during the response time period (see, for example, region 134 of FIG. 12). In other words, as shown in FIG. 11B, thermal image data is received for at least a region of a person's face during a question period of time and a time period during a response to the question (block 120). The thermal image data is transformed to determine the change of blood flow over time as shown in block 122 for the person during both such periods of time to provide a product slope of the question and answer time periods.

A product slope threshold is generated (block 124). The product slope threshold is generated using the slope representative of the change of the blood flow rate over time for a plurality of subjects, both non-deceptive and deceptive, during both the question period of time and the response period of time. In other words, as described above, the slope representative of the change of blood flow rate over time for each person during the question time period is multiplied times the slope representative of the change of blood flow rate over time for the person during the response time period to obtain a product slope. A thresholding algorithm such as that described above is applied to the product slopes to obtain the product slope threshold.

Thereafter, a binary decision is made with regard to the response to the question and the elicited response is determined as being deceptive or non-deceptive based on the product slope threshold (block 126). In other words, the product slope for a person is compared to the product slope threshold to classify a response from the person as deceptive or non-deceptive.

Although various exemplary processes have been provided as illustrative embodiments for classifying an individual as providing a deceptive or non-deceptive response to a question, one skilled in the art will readily recognize that other classification processes using blood flow rate data obtained from thermal image data of the human face 32 may be used according to the present invention.

One or more of the above methods and/or processes may be further understood by way of the following Example provided below.

EXAMPLE

Polygraph tests were designed around a mock crime scenario. The crime scene involved the stabbing of a woman with a screwdriver. Some of the subjects were programmed "innocent" and some were programmed "guilty." The guilty subjects enacted the crime as if it were real. A mannequin played the role of the stabbed woman in the crime scene. The theft of a $20 bill has been identified as the motive for the crime. The innocent subjects did not have any knowledge or association with the crime scene.

There were two sets of questions the subjects had to address: 10 full questions composing the so-called Zone Comparison Test (see Table 1) and 6 short questions composing the so-called Guilty Knowledge Test (GKT Test) (see Table 2). In the Zone Comparison Test, the subject was required to answer each question with a simple "yes" or "no." In the GKT Test, the subject had to read through a list of potential murder weapons, only one of which was the murder weapon pertaining to the case. His/her physiological response was gauged for each word. In traditional polygraph testing, a strong physiological response is anticipated when a guilty subject hears the murder weapon word.

TABLE 1

The 10 Zone Comparison Test questions used in the polygraph test.

| | Zone Comparison Test | Comment |
|---|---|---|
| 1 | Is your name _____ ? | Irrelevant - not scored |
| 2 | Regarding whether you stabbed that woman today, do you intend to answer any questions truthfully? | Sacrifice relevance - scored |
| 3 | Do you understand that I will not ask any trick or surprise questions on this test? | Symptomatic - not scored |

TABLE 1-continued

The 10 Zone Comparison Test questions used in the polygraph test.

| | Zone Comparison Test | Comment |
|---|---|---|
| 4 | Before arriving at Fort Jackson, did you ever hurt someone who trusted you? | Comparison - scored |
| 5 | Did you stab that woman this morning/afternoon? | Relevant - scored |
| 6 | Before arriving at Fort Jackson, did you ever lose your temper when you shouldn't have? | Comparison - scored |
| 7 | Did you stab that woman downstairs this morning/afternoon? | Relevant - scored |
| 8 | Is there a question you are afraid I will ask about even though I said I would not? | Symptomatic - not scored |
| 9 | Before this year, did you ever take anything important that didn't belong to you? | Comparison - scored |
| 10 | Do you have that stolen $20 on you right now? | Relevant - scored |

First, the polygraph examiner runs through the two question sets just to have the subject familiarized with the content of the examination. The subject is not required to answer any of the questions at this point, and nothing is scored. Then, the examiner repeats the questions and the subject is required to answer this time. This is the first official "run." There are two more runs that follow. In all three runs, the Zone Comparison Test questions remain exactly the same. In the GKT questions, however, the position of the murder weapon word changes from run to run. The position of the murder weapon word in the first two runs of our testing is shown in Table 2.

TABLE 2

The first two runs of the GKT questions for our polygraph test.

| | GKT Questions - Run 1 | GKT Questions - Run 2 |
|---|---|---|
| 1 | Irrelevant | Irrelevant |
| 2 | Irrelevant | Screwdriver (murder weapon) |
| 3 | Irrelevant | Irrelevant |
| 4 | Irrelevant | Irrelevant |
| 5 | Screwdriver (murder weapon) | Irrelevant |
| 6 | Irrelevant | Irrelevant |

In traditional polygraphy, all three runs are scored. By looking into the details of the scoring scheme, however, it is noticed that 3 questions in the Zone Comparison Test are never scored (see Table 1). These are either irrelevant or symptomatic questions and serve as fillers from the psychological point of view. The rationale for having the subject going 3 times through the Zone Comparison and GKT tests is to average the contribution of a possible noisy response. Of course, the average intensity of the physiological response is expected to be lower for runs 2 and 3 with comparison to run 1. This is attributable to the repetitive nature of the exercise and is taken into account in the scoring scheme.

Alongside the traditional invasive measurements, digital clips of thermal video data for each question of each subject were recorded. Our recording started right before the examiner expressed the question until right after the subject was done giving his/her answer. For the Zone Comparison Test questions, the average recording length was 300 frames at 30 frames/sec. For the GKT questions, the average recording length was 150 frames at 30 frames/sec. One of the most important questions for the determination of guilt or innocence was Question 10 (Q10), which in our case was phrased: "Do you have that stolen $20 on you right now?" Only the first two runs were recorded for thermal image processing and analysis.

A cooled mid-infrared camera, the Radiance HS by Raytheon, was used. The Focal Plane Area (FPA) of the camera is sensitive to the 3–5 µm waveband, and its size is 256×256 pixels.

Temperature sensitivity is important since only subtle stimuli within the mock crime context and consequently infinitesimal facial temperature changes occur. The thermal sensitivity of the Raytheon Radiance HS is NEDT=0.025° C.

To ensure the highest level of temperature reading accuracy, the Raytheon Radiance HS camera was calibrated using an external black body. Specifically, the 2008 Model by Santa Barbara Infrared with thermal sensitivity equivalent to that of our camera (NEDT=0.025° C.) was used. The minimum and maximum calibration temperatures were set to $T_{min}$=29° C. and $T_{max}$=38° C., respectively. Based on our experimental experience, these are the temperature extremities one can find across the human face.

Since operation was in the mid-infrared spectrum, to eliminate any effect on the measurements from illumination, the experiments were performed in a dimly lit room. The thermal camera was connected and controlled by a personal computer and associated software. Every video clip per question and subject was recorded directly on the hard disk.

In the polygraph test setting one could visually observe that the temperature changes around the eyes and in the face in general were very subtle, almost unnoticable as previously described herein with reference to FIGS. 5A–5B. FIG. 5A is representative of a raw thermal snapshot of subject 3 answering Question 10 (towards the beginning) and FIG. 5B is representative of a raw thermal snapshot of subject 3 answering Question 10 (towards the end). The difference between the two images cannot be perceived.

The thermal image data was transformed using the equation:

$$\frac{dV_S}{dt} = \frac{T_B(C_S + K_c/(3d)) - C}{(T_B - T_S)^2} \frac{dT_S}{dt}$$

By solving this equation for every pixel in the image, the raw thermal data can be transformed to blood flow rate data. To ensure a meaningful application of the equation, the image can be cropped so that it contains only the subject's face and no background. The cropping was performed at the first frame of each video clip and cropping dimensions applied across the timeline to the end of a particular question-answer session. This assumes a stationary subject for the short duration (5–10 seconds) of the question-answer session. Based on experimental experience, the stationary subject assumption is valid, although some agitated subjects moving noticeably during such short periods of time may affect some determinations.

Transformed data is represented in FIGS. 6A and 6B herein. FIG. 6A is visualization of the blood flow rate in subject 3's face as he answers Question 10 (towards the beginning). FIG. 6B is visualization of the blood flow rate in subject 3's face as he answers Question 10 (towards the end). The difference between the two images is significant. The shading indexes the range of the blood flow rate intensities from the lowest to the highest value.

The periorbital and forehead areas for each subject in each question were allowed to be delineated. The delineation takes place on the first frame of the video clip and is also based on the stationary subject assumption. Within the delineated periorbital and forehead areas, the respective average blood flow rate for each frame is computed. This produced two signals across the question timeline: one 'eye' signal and one 'forehead' signal. Such signals were input to the pattern recognition algorithm for subject classification to the deceptive or non-deceptive category.

It was determined that only the "eye" signals in the Zone Comparison Test carried significant discriminating power in this Example. One important restriction was that the subjects should not wear eyeglasses during the examination. Glass is opaque in the mid- and far-infrared, and therefore, may clutter the periorbital thermal signature. This restriction is easy to enforce in the controlled environment associated with polygraph testing.

The "forehead" signals (e.g., from region 37 as shown in FIG. 3) did not appear as discriminating and had other associated problems such as hair banks falling off the forehead of the subject resulting in the cluttering of the thermal signature of the underlying skin.

A careful visual observation of the "eye" signals revealed that there are two stages of physiological response in a question-answer session for a subject. This can be seen in FIG. 12. Initially, during the posing of the question in region 132, the "eye" curves ascend moderately for all subjects. Then, as the subjects respond to the question in region 134, there seems to be a differentiation: the "eye" curves of some subjects continue to ascend moderately (curves 138), while the "eye" curves of others feature a much steeper ascent (curves 136). The steep "eye" curves 136 during the answer session are indicative of a deceptive answer.

FIG. 12 shows the eye curves for all subjects for Question 10 (Q10) in run 1. During question posing (up to frame 150), there is little differentiation in the slope of the curves. During answer giving (from frame 151 up to frame 300), there is significant differentiation in the slope of the curves.

The "eye" curves appear to start from 0 because the initial conditions were zeroed for the solution of the differential equation computed. In other words, the measurements are to be interpreted in a comparative setting, since only a "dead subject" has zero initial blood flow rate. This comparative measurement setting is adequate for polygraph testing purposes, since one is only interested in the relative rate of ascend for the "eye" curves.

The product of the slopes of the "eye" curves in the corresponding question (region 132 of FIG. 12) and answer (region 134) sessions was used as the feature for classification. Ideally, the slope products should form a bi-modal distribution; one for the non-deceptive subjects and one for the deceptive subjects. The slope products are fed into a thresholding algorithm. Then, the threshold is used to make binary decisions. If the slope product of an "eye" curve is smaller than the threshold, then we classify the answer as non-deceptive. If the slope product of an "eye" curve is larger than the threshold, then we classify the answer as deceptive.

The thresholding algorithm selected is that described in the article by Otsu previously cited herein because of its performance in bi-modal distributions. It involves a non-parametric and unsupervised method of threshold selection. An optimal threshold is selected in order to maximize the separability of the resultant classes. The algorithm utilizes only the zeroth- and the first-order cumulative moments of the histogram. The classification results are presented below.

A set of 32 polygraphy subjects were examined. Data from only 22 of those were deemed legitimate for use; others were lost due to human and machine errors or contamination. From the 22 admissible subjects, 4 subjects were excluded because their polygraph examination took place immediately after lunch.

For all the 18 down-selected subjects, scores through thermal image analysis were only possible for Question 10 (Q10) of the Zone Comparison Test. However, Question 10 (Q10) is one of the most important questions in the determination of guilt or innocence for a subject and, therefore, the validity of our results remains quite relevant.

Table 3 shows the classification results by the thermal image analysis system vis-a-vis those by traditional polygraph analysis. One finds that our thermal image analysis method achieved correct classification rate (CCR)=84 percent (i.e., subjects having slope products of 67 degrees and above being correctly classified as being deceptive except for the false alarm of Subject 13; further, Subjects 14 and 17 were missed or in other words not detected when they should have been), while the traditional analysis achieves a CCR= 78 percent characterized by some false alarms and missed detections (i.e., subjects 17 and 6 being missed or in other words not detected when they should have been; Subjects 23 and 9 being false alarms or labeled as deceptive when they should not have been).

The feature for the classification is the product of slopes of the "eye" curve during the question and answer sessions for Question 10 (Q10) of the Zone Comparison Test. The slopes are expressed as the angle of the curve (in (ml/min*10 g)/frames) at frames 0 and 151, respectively (see FIG. 12). The list of product slopes is ordered from the minimum to the maximum value. Small slope product values correspond to non-deceptive answers, while large slope product values correspond to deceptive answers. All the deceptive cases are clustered at the bottom of the ordered list. The traditional scale ranges from −5 to +5, where non-negative values denote non-deceptive answers, while negative values indicate deceptive answers.

TABLE 3

| Thermal Scoring | | Traditional Scoring | |
| --- | --- | --- | --- |
| Subject | Slope Product | Subject | Deceptive Index |
| Subject 9 | 10.2 | Subject 13 | 4 |
| Subject 8 | 17.0 | Subject 25 | 3 |
| Subject 17 | 18.5 | Subject 8 | 2 |
| Subject 5 | 18.5 | Subject 12 | 2 |
| Subject 12 | 28.6 | Subject 17 | 2 |
| Subject 14 | 30.2 | Subject 18 | 2 |
| Subject 15 | 33.9 | Subject 5 | 1 |
| Subject 18 | 34.6 | Subject 6 | 0 |
| Subject 23 | 37.1 | Subject 10 | 0 |
| Subject 25 | 45.9 | Subject 15 | 0 |
| Subject 10 | 48.7 | Subject 21 | −1 |
| Subject 21 | 67.1 | Subject 23 | −1 |
| Subject 19 | 94.5 | Subject 3 | −2 |
| Subject 13 | 96.8 | Subject 9 | −2 |
| Subject 20 | 114.0 | Subject 14 | −2 |
| Subject 3 | 115.5 | Subject 20 | −2 |
| Subject 6 | 216.7 | Subject 19 | −3 |
| Subject 29 | 326.7 | Subject 29 | −3 |

By applying the thresholding algorithm by Otsu, as previously explained, a threshold value of T=67 degrees is attained. Using this value to make binary classification decisions, the decisions of Table 3 are achieved.

All references cited herein are incorporated in their entirety as if each were incorporated separately. This invention has been described with reference to illustrative embodiments and is not meant to be construed in a limiting sense. Various modifications of the illustrative embodiments, as well as additional embodiments of the invention, will be apparent to persons skilled in the art upon reference to this description.

What is claimed is:

1. A method for use in detecting deception of a person, the method comprising:

providing thermal image data of at least a region of a face of a person;

transforming the thermal image data to blood flow rate data, wherein the blood flow rate data comprises a slope representative of change of blood flow rate over time;

providing a slope threshold representative of a demarcation between change of blood flow rate over time for a deceptive person and change of blood flow rate over time for a non-deceptive person; and comparing the slope representative of change of blood flow rate over time to the slope threshold to determine whether the person is deceptive or non-deceptive.

2. The method of claim 1, wherein providing a slope threshold comprises generating a slope threshold based on at least answer slopes representative of the change of blood flow rate over time for a plurality of subjects during at least a portion of an answer period of time in which the plurality of subjects answer questions posed thereto.

3. The method of claim 1, wherein providing a slope threshold comprises generating a slope threshold based on answer slopes representative of the change of blood flow rate over time for a plurality of subjects during at least a portion of an answer period of time in which the plurality of subjects answer questions posed thereto during a question period of time and also based on question slopes representative of the change of blood flow rate over time for a plurality of subjects during at least a portion of the question period of time.

4. The method of claim 3, wherein providing a slope threshold comprises generating a slope threshold based on a product of corresponding question and answer slopes.

5. The method of claim 1, wherein providing the thermal image data comprises providing thermal image data of at least a region proximate an eye of the person.

6. The method of claim 1, wherein providing thermal image data comprises:

asking the person a question to elicit a response therefrom;

focusing a thermal infrared image device operable to provide thermal image data on at least the region of the face of the person; and capturing thermal image data during at least a period of time during the response from the person.

7. The method of claim 6, wherein determining whether the person is deceptive or non-deceptive comprises determining whether the person is being deceptive or non-deceptive with respect to the response to the question.

8. The method of claim 1, wherein providing thermal image data comprises:

focusing a thermal infrared image device operable to provide thermal image data on at least the region of the face of the person;

capturing frames of thermal image data during at least a period of time; and tracking movement of at least the region of the face of the person.

9. A system for use in detecting deception of a person, the system comprising:

a thermal infrared image device operable to provide thermal image data of at least a region of a face of a person; and a computing apparatus operable to:

transform the thermal image data to blood flow rate data, wherein the blood flow rate data comprises a slope representative of change of blood flow rate over time;

provide a slope threshold representative of a demarcation between change of blood flow rate over time for a deceptive person and change of blood flow rate over time for a non-deceptive person; and compare the slope representative of change of blood flow rate over time for a person to the slope threshold to determine the person as deceptive or non-deceptive.

10. The system of claim 9, wherein the slope threshold is provided based on at least answer slopes representative of the change of blood flow rate over time for a plurality of subjects during at least a portion of an answer period of time in which the plurality of subjects answer questions posed thereto.

11. The system of claim 9, wherein the slope threshold is provided based on answer slopes representative of the change of blood flow rate over time for a plurality of subjects during at least a portion of an answer period of time in which the plurality of subjects answer questions posed thereto during a question period of time and also on question slopes representative of the change of blood flow rate over time for a plurality of subjects during at least a portion of the question period of time.

12. The system of claim 11, wherein the slope threshold is based on a product of corresponding question and answer slopes.

13. The system of claim 9, wherein the thermal infrared image device is operable to provide thermal image data of at least a region proximate an eye of the person.

14. The system of claim 9, wherein the thermal infrared image device is operable to capture thermal image data during at least a period of time during at least an elicited response from the person.

15. The system of claim 14, wherein the computing apparatus is operable to determine whether the person is deceptive or non-deceptive based on the blood flow rate data corresponding to the thermal image data captured during at least the elicited response.

16. The system of claim 9, wherein the thermal infrared image device is operable to capture frames of thermal image data during at least a period of time, and further wherein the computing apparatus is further operable to track movement of at least the region of the face of the person during the period of time.

17. The system of claim 9, wherein the system further comprises means for providing measurement of one or more physiological parameters different than blood flow rate data obtained using thermal image data, and further wherein the computing apparatus is operable to determine whether the person is deceptive or non-deceptive based on the blood flow rate data obtained using thermal image data and the one or more physiological parameters.

18. A polygraph method for use in determining whether a person is being deceptive or non-deceptive with respect to a response elicited from the person, the method comprising:

capturing thermal image data from at least one region of the face of the person during at least the elicited response;

transforming the thermal image data to blood flow rate data, wherein the blood flow rate data comprises a slope representative of change of blood flow rate over time in the at least one region of the face;

providing a slope threshold representative of a demarcation between change of blood flow rate over time for a deceptive person and change of blood flow rate over time for a non-deceptive person; and comparing the slope representative of change of blood flow rate over time for the person to the slope threshold to classify the person's elicited response as deceptive or non-deceptive.

19. The method of claim 18, wherein providing a slope threshold comprises generating a slope threshold based on at least answer slopes representative of the change of blood flow rate over time for a plurality of subjects during at least a portion of an answer period of time in which the plurality of subjects answer questions posed thereto.

20. The method of claim 18, wherein providing a slope threshold comprises generating a slope threshold based on answer slopes representative of the change of blood flow rate over time for a plurality of subjects during at least a portion of an answer period of time in which the plurality of subjects answer questions posed thereto during a question period of time and also based on question slopes representative of the change of blood flow rate over time for a plurality of subjects during at least a portion of the question period of time.

21. The method of claim 20, wherein providing a slope threshold comprises generating a slope threshold based on a product of corresponding question and answer slopes.

22. The method of claim 18, wherein capturing the thermal image data comprises capturing thermal image data of at least a region proximate an eye of the person.

23. The method of claim 18, wherein the method further comprises providing measurement of one or more physiological parameters different than blood flow rate data obtained using thermal image data, and further wherein classifying the person elicited response as deceptive or non-deceptive comprises determining whether the person is deceptive or non-deceptive based on the blood flow rate data obtained using thermal image data and the one or more physiological parameters.

24. A method for use in determining a physiological state of a person, the method comprising:

providing thermal image data of at least a region of a face of a person;

transforming the thermal image data to blood flow rate data, wherein the blood flow rate data comprises a slope representative of change of blood flow rate over time;

providing a slope threshold representative of a demarcation between change of blood flow rate over time for a first physiological state of a person and change of blood flow rate over time for a second physiological state of a person; and comparing the slope representative of change of blood flow rate over time to the slope threshold to determine whether the person is in the first or second physiological state.

25. The method of claim 24, wherein the first physiological state of a person and the second physiological state of a person comprise a deceptive state and a non-deceptive state, respectively.

26. The method of claim 24, wherein providing the thermal image data comprises providing thermal image data of at least a region proximate an eye of the person.

27. The method of claim 24, wherein providing thermal image data comprises:

focusing a thermal infrared image device operable to provide thermal image data on at least the region of the face of the person;

capturing frames of thermal image data during at least a period of time; and tracking movement of at least the region of the face of the person.

28. A system for use in determining a physiological state of a person, the system comprising:

a thermal infrared image device operable to provide thermal image data of at least a region of a face of a person; and a computing apparatus operable to:

transform the thermal image data to blood flow rate data, wherein the blood flow rate data comprises a slope representative of change of blood flow rate over time;

provide a slope threshold representative of a demarcation between change of blood flow rate over time for a first physiological state of a person and change of blood flow rate over time for a second physiological state of a person; and compare the slope representative of change of blood flow rate over time to the slope threshold to determine whether the person is in the first or second physiological state.

29. The system of claim 28, wherein the first physiological state of a person and the second physiological state of a person comprise a deceptive state and a non-deceptive state, respectively.

30. The system of claim 28, wherein the thermal infrared image device is operable to provide thermal image data of at least a region proximate an eye of the person.

31. The system of claim 28, wherein the thermal infrared image device is operable to capture frames of thermal image data during at least a period of time, and further wherein the computing apparatus is further operable to track movement of at least the region of the face of the person during the period of time.

* * * * *